(12) United States Patent
D'Arbigny et al.

(10) Patent No.: US 7,838,009 B2
(45) Date of Patent: Nov. 23, 2010

(54) USE OF BOTULINUM TOXIN FOR THE PREPARATION OF A MEDICAMENT FOR THE TREATMENT OF LITHIASIS OF SALIVARY GLAND, GALL BLADDER, KIDNEY, OR PANCREAS

(75) Inventors: Pierre Bernard D'Arbigny, Courbevoie (FR); Piere-Etienne Chabrier De Lassauniere, Paris (FR); Alan Barcock, Berkshire (GB)

(73) Assignees: Ipsen Pharma S.A.S., Boulogne Billancourt (FR); Ipsen Biopharm Limited, Wrexham (GB)

( * ) Notice: Subject to any disclaimer, the term of this patent is extended or adjusted under 35 U.S.C. 154(b) by 0 days.

(21) Appl. No.: 11/632,222

(22) PCT Filed: Jul. 6, 2005

(86) PCT No.: PCT/GB2005/002659

§ 371 (c)(1),
(2), (4) Date: Jan. 8, 2008

(87) PCT Pub. No.: WO2006/005912

PCT Pub. Date: Jan. 19, 2006

(65) Prior Publication Data

US 2008/0292661 A1    Nov. 27, 2008

(30) Foreign Application Priority Data

Jul. 12, 2004    (GB) .................. 0415490.2

(51) Int. Cl.
*A61K 39/02*    (2006.01)
*A61K 39/08*    (2006.01)

(52) U.S. Cl. .............. 424/236.1; 424/247.1; 424/234.1; 424/239.1

(58) Field of Classification Search ................ None
See application file for complete search history.

(56) References Cited

U.S. PATENT DOCUMENTS

| 5,437,291 | A | 8/1995 | Pasricha et al. ............ 128/898 |
| 5,766,605 | A | 6/1998 | Sanders et al. ............. 424/239 |
| 6,143,306 | A | 11/2000 | Donovan .................... 424/236 |
| 2004/0086532 | A1 | 5/2004 | Donovan .................... 424/239 |
| 2005/0049175 | A1 | 3/2005 | Schmidt ........................ 514/2 |

FOREIGN PATENT DOCUMENTS

| AF | 1246634 | B1 | 12/2003 |
| WO | WO00/01238 | | 1/2000 |
| WO | WO2004/043430 | | 5/2004 |

*Primary Examiner*—S. Devi
(74) *Attorney, Agent, or Firm*—Jacobson Holman PLLC

(57) ABSTRACT

The invention relates to the use of a pre-synaptic neuromuscular blocking substance for preparing a medicament intended to treat a gland, organ or duct obstructed by a naturally formed stone. This method can be applied notably for salivary gland, gall bladder, kidney or pancreas stones.

5 Claims, No Drawings

USE OF BOTULINUM TOXIN FOR THE PREPARATION OF A MEDICAMENT FOR THE TREATMENT OF LITHIASIS OF SALIVARY GLAND, GALL BLADDER, KIDNEY, OR PANCREAS

This application is a national stage application of PCT/GB2005/002659 filed 6 Jul. 2005 and published in English, which claims foreign priority to application 0415490.2 filed Jul. 12, 2004 in the United Kingdom.

BACKGROUND OF THE INVENTION

1. Field of the Invention

The invention relates to the use of a pre-synaptic neuromuscular blocking substance for treating certain salivary gland, gall bladder, kidney and pancreas disorders.

2. Description of Related Art

Stones are often formed from residues in the salivary glands, gall bladder, kidneys and pancreas. If natural evacuation of these stones is not possible, the preferred treatments involve extracorporeal shock wave lithotripsy (which consists in shattering the stone(s) with a shock wave produced outside the human body). However this type of treatment is usually thought to be likely to succeed only with stones smaller than 1.5 cm in diameter so that, for bigger stones, other methods involving anesthesia and/or even surgery remain the only solution.

Among pre-synaptic neuromuscular blocking substances can be mentioned in first instance botulinum toxins. Botulinum toxin is the most lethal natural biological agent known to man. About 50 picograms of a commercially available botulinum toxin type A (purified neurotoxin complex) correspond to the $LD_{50}$ in mice. However, the same toxin has been used at tiny doses for therapeutic purposes in man since the 1980s. To date, it is believed to treat a number of disorders among which can be mentioned the following: blepharospasm, hemifacial spasm, cervical dystonia, cerebral palsy, post-stroke spasticity of the arm or leg, hyperhidrosis (e.g. palmar hyperhidrosis, axillar hyperhidrosis, Frey's syndrome or gustatory sweating), wrinkles (e.g. glabellar lines), urinary retention, urinary incontinence, benign prostatic hyperplasia, anal fissure, skin wounds, type 2 diabetes, articular pathologies, acne and many others.

Other botulinum toxins share the same therapeutic properties of botulinum toxin type A (e.g. botulinum toxins of types B, $C_1$, D, E, F and G); however, only botulinum toxin type A and botulinum toxin type B are currently marketed. Botulinum toxin type A is mainly commercially available from Ipsen (Dysport®, Ipsen Limited, Slough, UK) and Allergan (BOTOX®, Allergan Inc., Irvine, Calif., USA) whereas botulinum toxin type B is sold by Elan/Solstice Neurosciences (Myobloc®/Neurobloc®, Elan Pharmaceuticals Inc., South San Francisco, Calif., USA; Solstice Neurosciences, Inc., San Diego, Calif., USA).

Besides, U.S. Pat. No. 5,766,605 teaches the administration of botulinum toxin to the salivary glands for treating excessive salivation and European patent EP 1 246 634 teaches the local administration of botulinum toxin to the pancreas for treating pancreatic disorders such as pancreatitis and endocrine pancreatic disorders such as hypoglycaemic hyperinsulinism or hyperglycaemic hyperglucagonism.

Summary of the Invention

The Applicant has now surprisingly found that a pre-synaptic neuromuscular blocking substance, and in particular a botulinum toxin, could also be used for the treatment of glands, organs or ducts obstructed by naturally formed stones (e.g. salivary glands, gall bladder, kidneys or pancreas obstructed by stones).

By "naturally formed stone" is meant any stone formed within a gland, organ or duct due to the aggregation of solid particles.

According to the invention, the pre-synaptic neuromuscular blocking substance is administered locally in an effective amount to the obstructed gland or organ (e.g. obstructed salivary gland, gall bladder, kidney or pancreas).

Detailed Description of the Invention

By pre-synaptic neuromuscular blocking substance should be understood in the present application a substance that prevents and/or inhibits transmission of the chemical messages and signals involved in pre-synaptic neuromuscular activity. Examples of such pre-synaptic neuromuscular blocking substances are substances that inhibit acetylcholine (ACh) synthesis or release; those include notably biological toxins (such as botulinum neurotoxins and bungarotoxins but also any synthetic analogue thereof having the same activity like recombinantly engineered botulinum toxins) and chemicals (such as hemicholinium or triethylcholine which inhibit ACh synthesis, aminoglycoside antibiotics which inhibit ACh release or tubocurarine and similar compounds). Preferred pre-synaptic neuromuscular blocking substances according to this invention will be botulinum neurotoxins and bungarotoxins (α-bungarotoxin being preferred among the bungarotoxins).

By botulinum neurotoxins (or botulinum toxins) is meant in the present application botulinum neurotoxin complexes (whether of type A, B, C, D, E, F, G or others), high purity botulinum neurotoxins (whether of type A, B, C, D, E, F, G or others) as well as any recombinantly engineered botulinum toxin having similar or better properties than the naturally occurring botulinum toxins or the purified forms thereof. Botulinum toxin type A includes all types of botulinum toxin type A, including $A_1$, $A_2$ and $A_3$, botulinum toxin type C includes all types of botulinum toxin type C, including $C_1$ or $C_2$; the same applies mutatis mutandis to the other serotypes of toxins.

By botulinum neurotoxin complex (whether of type A, B, C, D, E, F, G or others) should be understood in the present application a botulinum neurotoxin (whether of type A, B, C, D, E, F, G or others) associated with at least another non-toxic protein.

By high purity botulinum neurotoxin (whether of type A, B, C, D, E, F, G or others) is meant, in the present application, botulinum neurotoxin (whether of type A, B, C, D, E, F, G or others) outside from complexes including at least another protein. In other words, a high purity botulinum neurotoxin (type A, B, C, D, E, F, G or others) does not contain significant quantities of any other *Clostridium* spp derived protein than botulinum neurotoxin (type A, B, C, D, E, F, G or others).

As used herein, "local administration" means direct injection of a solution or suspension containing the pre-synaptic neuromuscular blocking substance into the obstructed gland or organ (which may in particular be a salivary gland, the gall bladder, a kidney or the pancreas), administration of said solution or suspension in close vicinity of the obstructed gland or organ (i.e. less than 2 or 3 cm from said gland or organ) or instillation or spraying of a solution or suspension containing said pre-synaptic neuromuscular blocking substance into the obstructed gland or organ by means of a catheter/endoscope device introduced through the natural routes (e.g. urethra and ureter for the kidney, bile duct for the gall bladder, pancreatic duct for the pancreas). Local administration by injection may involve the use of a catheter/endoscope device and the use of video equipment or some other type of control (e.g. echography control).

Therefore, the invention relates to the use of a pre-synaptic neuromuscular blocking substance for preparing a medicament intended to treat gland or organ stones such as salivary gland, gall bladder, kidney and pancreas stones.

Hence, according to a first particular aspect of the invention, the pre-synaptic neuromuscular blocking substance will be used for preparing a medicament intended to treat salivary gland stones; according to a second particular aspect of the invention, the pre-synaptic neuromuscular blocking substance will be used for preparing a medicament intended to treat gall bladder stones; according to a third particular aspect of the invention, the pre-synaptic neuromuscular blocking substance will be used for preparing a medicament intended to treat kidney stones; and according to a fourth particular aspect of the invention, the pre-synaptic neuromuscular blocking substance will be used for preparing a medicament intended to treat pancreatic duct stones.

Preferably, the pre-synaptic neuromuscular blocking substance will be a botulinum toxin. More preferably, the botulinum toxin will be selected from the group consisting of botulinum toxin type A, botulinum toxin type B and botulinum toxin type F. Even more preferably, the botulinum toxin will be selected from the group consisting of botulinum toxin type A and botulinum toxin type B. In particular, the botulinum toxin will be botulinum toxin type A.

The effective amount of pre-synaptic neuromuscular blocking substance varies depending on the disorder to be treated, the age and body weight of the subject to be treated, as well as the state of the latter, and will be finally decided by the attending doctor or veterinarian.

However, it is believed that this effective amount could be as follows for botulinum toxin type A:
for salivary gland obstruction, from 0.1 to 1000 Ipsen units, preferably from 1 to 500 Ipsen units and more preferably from 10 to 200 Ipsen units (e.g. from 50 to 150 Ipsen units);
for gall bladder obstruction, from 0.1 to 1000 Ipsen units, preferably from 1 to 500 Ipsen units and more preferably from 10 to 300 Ipsen units (e.g. from 50 to 250 Ipsen units);
for kidney obstruction, from 0.1 to 1000 Ipsen units, preferably from 1 to 500 Ipsen units and more preferably from 10 to 350 Ipsen units (e.g. from 50 to 300 Ipsen units);
for pancreatic obstruction, from 0.1 to 1000 Ipsen units, preferably from 1 to 500 Ipsen units and more preferably from 10 to 350 Ipsen units (e.g. from 50 to 300 Ipsen units).

The approximate effective amounts for the other pre-synaptic neuromuscular blocking substances can easily be deduced by one skilled in the art (by a conversion based on his knowledge of the respective activities of said substances).

Concerning salivary gland stones, the pre-synaptic neuromuscular blocking substance is intended to be administered by intraglandular and/or extraglandular injection(s) close to the gland tissues and/or into the salivary duct.

Concerning gall bladder stones, the pre-synaptic neuromuscular blocking substance is intended to be administered by intraglandular and/or extraglandular injection(s) close to the gall bladder tissues and/or into the bile duct.

Concerning pancreatic duct stones, the pre-synaptic neuromuscular blocking substance is intended to be administered by intraglandular and/or extraglandular injection(s) close to the pancreatic tissues and/or into the pancreatic duct.

In all the preceding instances, the treatment offers the benefits of pain, inflammation and/or gland swelling reduction as well as facilitation of stone evacuation by natural route (or of extracorporeal shock wave lithotripsy and/or surgical access if necessary).

Concerning kidney stones, the pre-synaptic neuromuscular blocking substance is intended to be administered by injection(s) in the kidney tissues and/or close to the kidney tissues and/or into the ureter. In this instance, the treatment offers the benefits of pain, inflammation swelling, reduction and/or bleeding as well as facilitation of stone evacuation by natural route (or of extracorporeal shock wave lithotripsy and/or surgical access if necessary).

According to a preferred variant of the invention, the pre-synaptic neuromuscular blocking substance treatment will prepare the patient for ultrasonic treatment and/or surgical procedure. In other words, a further aspect of the invention is the use of a pre-synaptic neuromuscular blocking substance for preparing a medicament intended to treat a gland, organ or duct obstructed by a naturally formed stone, wherein said medicament is intended to be administered before an extracorporeal shock wave lithotripsy and/or a surgery (e.g. in preparation of an extracorporeal shock wave lithotripsy and/or a surgery).

The botulinum toxin treatment may optionally be associated with an analgesic treatment (e.g. by administration of morphine) between the moment at which the toxin is administered and the moment at which the affected gland or organ is freed from the obstructing stone.

The term "about" refers to an interval around the considered value. As used in this patent application, "about X" means an interval from X minus 10% of X to X plus 10% of X, and preferably an interval from X minus 5% of X to X plus 5% of X.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following examples are presented to illustrate the above and must in no case be considered as a limit to the scope of the invention.

EXAMPLES

Example 1

Treatment of Gall Bladder Stones

A female patient in her late forties is diagnosed with a gall bladder stone of about 1.1 cm of diameter associated with clinical symptoms including moderate pain. An endoscope fitted with both a video camera and an injection system is introduced through the gall bladder duct and injection of a total dose of 200 units of a botulinum toxin type A preparation (e.g. Dysport® from Ipsen Ltd, Slough, UK—the product being used following the reconstitution protocol of the manufacturer) is carried out in the gall bladder wall and duct. About 5-6 days afterwards, the symptoms are relieved. The total evacuation of the stone is confirmed by echography two weeks after treatment.

Example 2

Treatment of Gall Bladder Stones

A male patient in his mid-fifties is diagnosed with a gall bladder stone of about 1.5 cm of diameter associated with clinical symptoms including pain. An endoscope fitted with both a video camera and an injection system is introduced through the gall bladder duct and injection of a total dose of 230 units of a botulinum toxin type A preparation (e.g. Dysport® from Ipsen Ltd, Slough, UK—the product being used following the reconstitution protocol of the manufacturer) is carried out in the gall bladder wall and duct. Extracorporeal shock wave lithotripsy is scheduled and performed two weeks after botulinum toxin treatment. Evacuation of the stone fragments was easy and not painful.

Example 3

Treatment of Salivary Gland Stones

A male patient in his fifties is diagnosed with a large salivary gland stone of about 14 mm length and 9 mm diameter in the submandibular gland confirmed by X-ray. Swelling and inflammation of the gland are observed. Access to the submandibular salivary gland is by the mouth of the patient and an injection of a total dose of 125 units of a botulinum toxin type A preparation (e.g. Dysport® from Ipsen Ltd, Slough, UK—the product being used following the reconstitution protocol of the manufacturer) is carried out. Regular massage of the gland was advised to compensate the expected decrease of secretion. Shortly afterwards, the patient experiences pain reduction and then, swelling and inflammation of the gland are significantly reduced. One week after the botulinum toxin treatment, the progression and eventual evacuation of the stone of the patient is confirmed by echography or X-ray.

Example 4

Treatment of Kidney Stones

A female patient in her late fifties is diagnosed with a kidney stone of about 9 mm associated with pain symptoms. A ureteroscope fitted with both a video camera and an injection system is introduced into the ureter and injection of a total dose of 125 units of a botulinum toxin type A preparation (e.g. Dysport® from Ipsen Ltd, Slough, UK—the product being used following the reconstitution protocol of the manufacturer) is carried out in the ureter. Decrease of pain and bleeding is noticed. A few days afterwards, the stone of the patient is expelled by the natural route as shown by echography.

Example 5

Treatment of Kidney Stones

A male patient in his late sixties is diagnosed with a kidney stone of about 1.8 cm associated with important pain symptoms justifying surgery decision. As an alternative, injection of a total dose of 250 units of a botulinum toxin type A preparation (e.g. Dysport® from Ipsen Ltd, Slough, UK—the product being used following the reconstitution protocol of the manufacturer) is carried out in the kidney and ureter with the assistance of a ureteroscope. Decrease of pain and bleeding is noticed. About one week afterwards, extracorporeal shock wave lithotripsy is performed and fragments of the stone of the patient are expelled by the natural route and filtered in the patient's urine.

Example 6

Treatment of Pancreatic Duct Stones

A male patient in his mid-fifties is diagnosed with a pancreatic duct stone of about 9 mm associated with significant pain symptoms. An endoscope fitted with both a video camera and an injection system is introduced into the pancreatic duct and injection of a total dose of 125 units of a botulinum toxin type A preparation (e.g. Dysport® from Ipsen Ltd, Slough, UK—the product being used following the reconstitution protocol of the manufacturer) is carried out in the pancreatic duct. Decrease of pain is noticed. A few days afterwards, the stone of the patient is expelled by the natural route as shown by echography.

The invention claimed is:

1. A method of treating a subject with a kidney obstructed by a naturally formed kidney stone or a subject with pancreas obstructed by naturally formed pancreatic duct stone, said method comprising direct injection of an effective amount of a solution or suspension of botulinum toxin into the obstructed kidney or the obstructed pancreas.

2. The method of claim 1, wherein the botulinum toxin is selected from the group consisting of botulinum toxin type A, botulinum toxin type B and botulinum toxin type F.

3. The method of claim 1, wherein the botulinum toxin is botulinum toxin type A.

4. The method of claim 1, wherein the subject has the naturally formed kidney stone.

5. The method of claim 1, wherein the subject has the naturally formed pancreatic duct stone.

* * * * *